United States Patent
Bezemer et al.

(10) Patent No.: US 10,863,966 B2
(45) Date of Patent: Dec. 15, 2020

(54) MONITORING APPARATUS FOR MONITORING BLOOD PRESSURE OF A SUBJECT

(71) Applicant: KONINKLIJKE PHILIPS N.V., Eindhoven (NL)

(72) Inventors: Rick Bezemer, Amsterdam (NL); Denny Mathew, Eindhoven (NL); Bart Kroon, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 359 days.

(21) Appl. No.: 15/751,981

(22) PCT Filed: Aug. 16, 2016

(86) PCT No.: PCT/EP2016/069445
§ 371 (c)(1),
(2) Date: Feb. 12, 2018

(87) PCT Pub. No.: WO2017/032648
PCT Pub. Date: Mar. 2, 2017

(65) Prior Publication Data
US 2018/0235567 A1   Aug. 23, 2018

(30) Foreign Application Priority Data
Aug. 21, 2015 (EP) .................... 15181917

(51) Int. Cl.
*A61B 8/04* (2006.01)
*A61B 5/021* (2006.01)
(Continued)

(52) U.S. Cl.
CPC ............ *A61B 8/04* (2013.01); *A61B 5/02007* (2013.01); *A61B 5/0261* (2013.01);
(Continued)

(58) Field of Classification Search
CPC .... A61B 8/04; A61B 8/06; A61B 8/42; A61B 8/4416; A61B 8/488; A61B 8/5261;
(Continued)

(56) References Cited

U.S. PATENT DOCUMENTS 6,331,162 B1   12/2001  Mitchell
2008/0039731 A1*  2/2008  McCombie ........ A61B 5/02125
                                         600/485

(Continued)

FOREIGN PATENT DOCUMENTS

EP     2049012       4/2009
WO   2013019991    2/2013
(Continued)

OTHER PUBLICATIONS

Rohan Anchan: "Estimating Pulse Wave Velocity using Mobile Phone Sensors", Jul. 31, 2011.
(Continued)

*Primary Examiner* — Amelie R Davis
*Assistant Examiner* — John Denny Li

(57) ABSTRACT

A monitoring apparatus for monitoring a blood pressure information of a subject is disclosed. The monitoring apparatus comprises an ultrasound transducer for emitting ultrasound waves to a volume of the subject that includes a blood vessel and for receiving ultrasound waves from said volume of the subject, and for providing a first signal on the basis of ultrasound waves received from the volume of the subject. A light source is included for emitting light to the subject and a light sensor is included for detecting light received from the subject and for providing a second signal on the basis of the light received from a skin of the subject. The monitoring apparatus comprises a processing unit for determining: i) a time of arrival of a cardiac pulse in the blood vessel based on the first signal, ii) a point in time when the
(Continued)

cardiac pulse reaches the skin of the subject based on the second signal, iii) a pulse transit time between the time of arrival of the cardiac pulse PPG in the blood vessel and the point in time when the cardiac pulse reaches the skin of the subject; and iv) the blood pressure based on the pulse transit time.

15 Claims, 6 Drawing Sheets

(51) Int. Cl.
*A61B 5/024* (2006.01)
*A61B 8/08* (2006.01)
*A61B 5/026* (2006.01)
*A61B 5/02* (2006.01)
*A61B 5/00* (2006.01)
*A61B 8/06* (2006.01)
*A61B 8/00* (2006.01)

(52) U.S. Cl.
CPC ...... *A61B 5/02125* (2013.01); *A61B 5/02416* (2013.01); *A61B 5/6832* (2013.01); *A61B 8/06* (2013.01); *A61B 8/42* (2013.01); *A61B 8/4416* (2013.01); *A61B 8/488* (2013.01); *A61B 8/5261* (2013.01); *A61B 2560/0223* (2013.01)

(58) Field of Classification Search
CPC ............ A61B 5/02007; A61B 5/02125; A61B 5/02416; A61B 5/0261; A61B 5/6832; A61B 2560/0223
See application file for complete search history.

(56) References Cited

U.S. PATENT DOCUMENTS

| | | |
|---|---|---|
| 2008/0082004 A1 | 4/2008 | Banet |
| 2008/0119741 A1* | 5/2008 | Friedman ........... A61B 5/02007 600/485 |
| 2009/0018409 A1 | 1/2009 | Banet |
| 2011/0224557 A1 | 9/2011 | Banet |
| 2013/0116663 A1 | 5/2013 | Baym |
| 2013/0137938 A1* | 5/2013 | Peters ................. A61B 5/0205 600/301 |
| 2013/0172691 A1 | 7/2013 | Tran |
| 2013/0296714 A1* | 11/2013 | Kassim ................ A61B 5/6898 600/479 |
| 2014/0107435 A1* | 4/2014 | Sharf ...................... A61B 8/06 600/301 |
| 2014/0187941 A1 | 7/2014 | Shusterman |

FOREIGN PATENT DOCUMENTS

| | | |
|---|---|---|
| WO | 2013/165474 | 11/2013 |
| WO | 2016180636 | 11/2016 |

OTHER PUBLICATIONS

Wang CZ, Zheng YP: "Comparison between reflection-mode photoplethysmography and arterial diameter change detected by ultrasound at the region of radial artery", Blood Pressure Monitoring, vol. 15, No. 4, Aug. 31, 2010.

Pereira T et al: "Correlation study between blood pressure and pulse transit time", 2015 IEEE 4th Portuguese Meeting on Bioengineering (ENBENG), IEEE, Feb. 26, 2015.

* cited by examiner

MONITORING APPARATUS FOR MONITORING BLOOD PRESSURE OF A SUBJECT

CROSS REFERENCE TO RELATED APPLICATIONS

This application is the U.S. National Phase application under 35 U.S.C. § 371 of International Application No. PCT/EP2016/069445, filed Aug. 16, 2016, published as WO 2017/032648 on Mar. 2, 2017, which claims the benefit of European Patent Application Number 15181917.4 filed Aug. 21, 2015. These applications are hereby incorporated by reference herein.

FIELD OF THE INVENTION

The present invention relates to a monitoring apparatus for monitoring vital sign information of a subject.
The present invention further relates to a monitoring method for monitoring vital sign information of a subject.
The present invention in particular relates to the determination of a blood pressure as the vital sign information of the subject.

BACKGROUND OF THE INVENTION

Blood pressure is an important vital sign information to monitor diseases of a patient. Common measurement methods are performed either discontinuously by means of a cuff, which is cumbersome and uncomfortable for the user or continuously by means of an arterial line, which is invasive and increases the risk of an infection. An alternative method for measuring the blood pressure non-invasively and continuously is based on the measurement of a pulse wave velocity, wherein the velocity at which a heartbeat-induced pressure pulse travels through the vasculation is determined, from which the blood pressure of the patient can be inferred.

The pulse wave velocity is commonly assessed by measuring a time delay between a heartbeat and the arrival of the pressure pulse in the skin, wherein the heartbeat is measured by means of electrocardiographic sensors disposed at the thorax of the patient. A corresponding blood pressure measurement system is e.g. known from US 2014/0187941 A1.

The known blood pressure measurement systems which monitor the blood pressure by determining the pulse arrival time utilize a plurality of electrocardiographic electrodes disposed on the chest and a photoplethysmography sensor at a finger, which require cable connections in order to evaluate the respective measurement signals, so that the known non-invasive blood pressure measurement systems require a large technical effort, are obstructive and uncomfortable for the user. Further, since the photoplethysmography sensor is disposed at a finger and the peripheral vascular resistance of the arms vary due to factors which are not related to the blood pressure, the measurement results have a reduced reliability.

Pereira, T. et al.: "*Correlation Study Between Blood Pressure and Pulse Transit Time*", 2015 IEEE 4$^{th}$ Portuguese Meeting on Bioengineering, pages 1-5 discloses a method for determining the blood pressure based on a pulse transit time that is measured by means of an ECG, multiple PPG sensors and an ultrasound system for measuring the artery diameter.

SUMMARY OF THE INVENTION

It is therefore an object of the present invention to provide an improved monitoring apparatus and a corresponding improved monitoring method for monitoring a blood pressure of a subject, which provides a reliable measurement of the blood pressure and which is comfortable for the user.

According to one aspect of the present invention, a monitoring apparatus for monitoring a blood pressure of a subject is provided, comprising:

an ultrasound transducer for emitting ultrasound waves to a volume of the subject that includes a blood vessel (such as an artery or a vein) and for receiving ultrasound waves from said volume of the subject and for providing a first signal on the basis of ultrasound waves received from the volume of the subject, a light source for emitting light to the subject and a light sensor for detecting light received from the subject and for providing a second signal on the basis of the light received from a skin of the subject, and a processing unit which is configured to:
   determine a time of arrival of a cardiac pulse in the blood vessel based on the first signal,
   determine a point in time when the cardiac pulse reaches the skin of the subject based on the second signal,
   determine a pulse transit time between the time of arrival of the cardiac pulse in the blood vessel and the point in time when the cardiac pulse reaches the skin of the subject; and
   determine the blood pressure based on the pulse transit time.

According to another aspect of the present invention, a monitoring method for monitoring a blood pressure of a subject is provided comprising the steps of:

determining a first signal on the basis of ultrasound waves received from a volume of the subject that includes a blood vessel (such as an artery or a vein), determining a second signal on the basis of a light received from a skin of the subject, determining a time of arrival of a cardiac pulse in the blood vessel based on the first signal;

determining a point in time when the cardiac pulse reaches the skin of the subject based on the second signal;

determining a pulse transit time between the time of arrival of the cardiac pulse in the blood vessel and the point in time when the cardiac pulse reaches the skin of the subject; and determining the blood pressure based on the pulse transit time.

Embodiments of the invention are defined in the dependent claims. It shall be understood that the claimed method has similar and/or identical preferred embodiments as the claimed device and as defined in the dependent claims.

The present invention is based on the idea to measure vital sign information of the subject, in particular the blood pressure by measuring a pulse transit time utilizing ultrasound measurements received from a volume of the subject and a light signal received from a portion of the subject, wherein the pulse transit time is determined on the basis of a comparison of a signal based on the ultrasound measurement and a signal based on the light measurement. Since both measurements can be performed at neighboring locations at the skin of the subject, e.g. a large artery, a large vein, the effort for the electrical connection of the sensors is reduced and the comfort for wearing the monitoring apparatus is increased. Further, since the ultrasound transducer and the light sensor can be placed close to each other at the same site of the subject, the influence of several parameter on the pulse transit time which dot not relate to the vital sign information to be measured, e.g. the blood pressure, can be reduced so that the reliability of the measurement can be increased.

The pulse transit time in accordance with the present description, and consequently to the present invention, is broadly defined and includes arterial pulse transit time and/or venous pulse transit time.

Hence, a reliable measurement of the vital sign information can be provided with less obtrusiveness and which is more comfortable for the user.

In an embodiment, the processing unit is adapted to determine a time delay between the first signal and the second signal and to determine the vital sign information on the basis of the time delay. This is a possibility to determine a pulse transit time of a pressure pulse of the subject reliable with low burden for the user.

In an embodiment, the ultrasound transducer and the light sensor are attached to a common base layer of the monitoring apparatus. This is a possibility to combine the ultrasound transducer and the light sensor in a single patch which can be placed at the skin of the subject to measure the vital sign information, so that the vital sign information can be measured more comfortable for the user.

In an embodiment, the light sensor is a photoplethysmography sensor for providing a photoplethysmography signal as the second signal to the processing unit. This is a possibility to determine the vital sign information reliable with low technical effort.

In a further embodiment, further characteristics of the first and the second signal like dc level, ac amplitude, ac/dc ratio, a peak/notch ratio, a time delay between peak and notch, features from the first and second derivatives, and features from the frequency spectrum can be measured to determine the vital sign information.

In an embodiment, the light source is adapted to emit light having different wavelengths and wherein the light sensor is adapted to detect the wavelengths backscattered by the portion of the subject. The light sensor is in particular adapted to detect the different wavelengths emitted by the light source and backscattered by the portion of the subject. This is a possibility to determine the blood oxygen level of the subject.

In a further embodiment, the ultrasound transducer is adapted to provide a blood velocity signal corresponding to a blood velocity in the volume of the subject on the basis of the ultrasound waves received from the subject as the first signal. The blood velocity is in particular determined based on an ultrasound Doppler signal received from a vessel of the subject. This is a possibility to determine a pulse transit time between a characteristic feature of the blood flow velocity and the light signal received from the portion of the subject with high reliability and low technical effort. The characteristic feature may be a peak, a foot, a rising or a falling slope in the blood velocity and the light signal.

In a further preferred embodiment, the ultrasound transducer is adapted to provide a movement signal corresponding to a movement of an anatomical feature in the volume of the subject as the first signal. In particular, the arrival of a pressure pulse is derived from an arterial wall movement which is preferably derived from fast sequential A-mode or B-mode images of the ultrasound transducer. This is a possibility to determine the timing of the arrival of the arterial pulse.

In an embodiment, the processing unit is adapted to determine an arterial stiffness on the basis of the blood velocity and the movement of the anatomical feature. The anatomical feature is preferably a wall of the respective artery. The so determined arterial stiffness can be utilized to improve the reliability of the determination of the blood pressure.

In a further embodiment, the vital sign information determined by the processing unit corresponds to a blood pressure of the subject. This is a possibility to determine the blood pressure of the subject reliable and comfortable for the user.

In a further embodiment, the blood pressure is determined on the basis of the time delay between the first signal and the second signal and a calibration function. This is a possibility to improve the blood pressure measurement.

In a further embodiment, the monitoring apparatus comprises a transmission unit connectable to the processing unit for transmitting the vital sign information to a base unit. This is a possibility to transmit the measurement results and to evaluate the measurement results and/or display the measurement results to the user or a third person.

In a further embodiment, the monitoring apparatus comprises an acceleration detection unit for detecting a motion and/or an orientation or a posture of the monitoring apparatus and/or the subject, wherein the processing unit is adapted to determine the vital sign information at least partially on the basis of the detected motion and/or the detected orientation. This is a possibility to determine a change in the posture of the monitoring apparatus and/or the subject and to apply a correct calibration function so that the reliability of the measurement can be improved. In particular the posture of the monitoring apparatus and/or the subject with respect to gravity can be considered.

In an embodiment, the base layer comprises a glue layer or an adhesive layer for attaching the monitoring apparatus to a skin of the subject. This is a possibility to further reduce the handling effort, to improve the measurement stability, and to improve the comfort for the user, since the ultrasound transducer and the light sensor can be attached to the body of the subject and no additional sensors or cables are required.

In a further embodiment, the monitoring apparatus comprises a feedback unit for determining a contact of the base layer to the subject on the basis of the first signal and/or on the basis of the second signal. This is a possibility to automatically determine the quality of the contact of the base layer to the skin of the subject so that the reliability of the measurement can be further improved.

The monitoring apparatus may comprise one or more pressure transducer attached to the base layer for controlling or regulating the contact pressure of the light sensor and the ultrasound transducer to the skin of the subject. This is a possibility to improve the contact quality and the reliability of the measurement.

As mentioned above, the present invention provides a monitoring apparatus and a monitoring method which can measure a vital sign information of a subject with high reliability and improved comfort for the user, since a pulse transit time can be determined at a single site of the subject and/or neighbored portions of the subject the influence of other vital parameter on the determined vital sign information can be reduced. Further, the comfort can be improved since no additional sensors or cables are required. The monitoring apparatus and the monitoring method allow long time monitoring and the measurement of blood pressure trending.

The present document further contemplates a monitoring apparatus for monitoring vital sign information of a subject, comprising:

an ultrasound transducer for emitting ultrasound waves to a volume of the subject and for receiving ultrasound waves from said volume of the subject, and for providing a first signal on the basis of ultrasound waves received from the volume of the subject, a light source for emitting light to the subject and a light sensor for detecting emitted light received from the subject and for providing a second signal on the basis of the light received from a portion of the subject, and a processing unit for determining the vital sign information on the basis of the first signal and the second signal.

The monitoring apparatus of the preceding paragraph may comprise all alternatives embodiment as the monitoring apparatus of claim 1 of the present document. A corresponding monitoring method is further contemplated, said monitoring method for determining vital sign information of a subject comprises the steps of:

determining a first signal on the basis of ultrasound waves received from a volume of the subject, determining a second signal on the basis of a light received from a portion of the subject, and determining the vital sign information on the basis of the first signal and the second signal.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
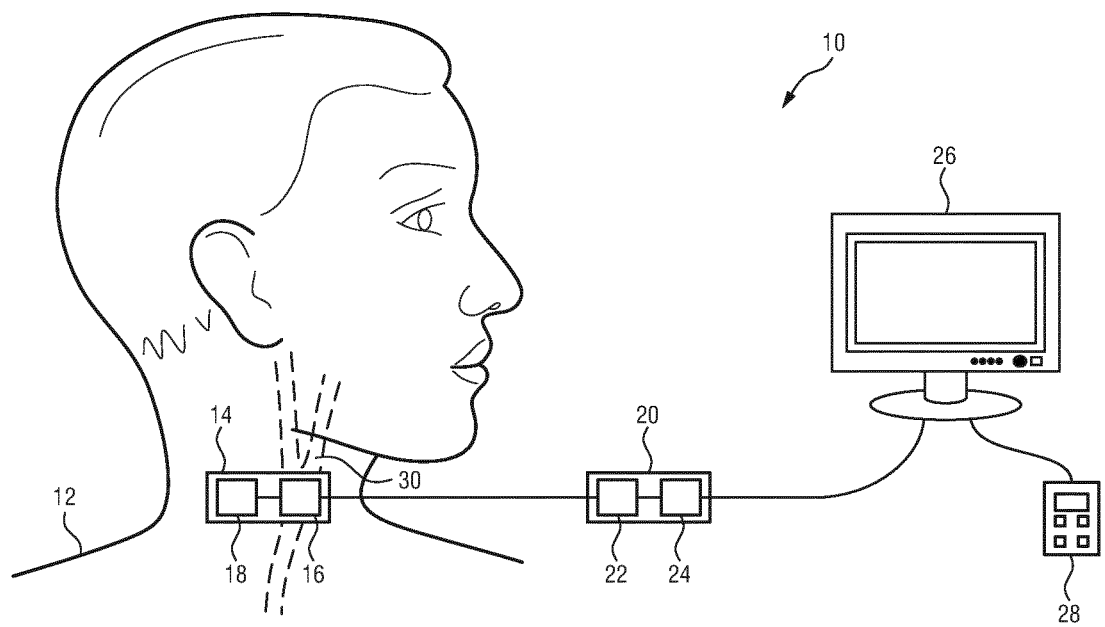
FIG. 1 shows a schematic representation of a monitoring apparatus for monitoring vital sign information of a subject.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

FIG. 1 shows a schematic illustration of a monitoring apparatus generally denoted by 10. The monitoring apparatus 10 is provided for monitoring vital sign information of a subject 12, in particular a patient 12. The monitoring apparatus comprises a measurement unit 14 having an ultrasound transducer 16 including one transducer element or a multitude of transducer elements for transmitting and receiving ultrasound waves. The multitude of transducer elements are preferably arranged in a 2D transducer array. The transducer elements are formed of piezoelectric transducer elements (PZT) or capacitive micromachined ultrasound transducer elements (CMUT) providing ultrasound waves in a range 2 to 20 megahertz. The transducer array can be used either for A-mode or B-mode operations as well as continuous waves or pulse wave Doppler operation.

The measurement unit 14 further comprises a light detection device 18 including a light source for emitting light and a light sensor for detecting the light of the light source backscattered from a portion of the subject 12. The light detection device 18 is preferably formed as a photoplethysmography sensor. The light emitted by the light source may be visible light and near-infrared light or green, red, and infrared light. The center wavelengths could be 530, 580, 600, 630, 780, 800, 880, 940, 1064 nm.

The monitoring apparatus 10 further comprises a control unit 20 comprising a controller 22 and a processing unit 24. The control unit 20 is connected or connectable to the measurement unit 14 by means of a cable connection or by means of a wireless connection, wherein the controller 22 receives measurement signals from the ultrasound transducer 16 and the light detection device 18 and controls the ultrasound transducer 16 and the light detection device 18 accordingly. The processing unit 24 receives the measurement signals from the ultrasound transducer 16 and the light detection device 18 and determines vital sign information of the subject 12 on the basis of the measurement signals as described in the following. The control unit 20 may be connected or connectable to an output device 26, e.g. a display device 26 and may be connected or connectable to an input device 28 which may be connected to the output device 26 or to the control unit 20 in order to control the acquisition of the measurement data. The output device 26 and the input device 28 may be connected to the control unit 20 by means of a cable connection or by means of a wireless connection.

The measurement unit 14 is attached to a skin of the subject 12 and formed e.g. by a wearable patch which is placed on the top of an artery 30 as shown in FIG. 1. The ultrasound transducer 16 measures an arrival of a cardiac pulse in the artery 30 either by determining a movement of a vascular wall or by determining a Doppler signal on the basis of the ultrasound waves received by the ultrasound transducer 16. The ultrasound transducer 16 provides a corresponding first signal to the processing unit 24.

The light detection device 18 detects light received from the skin of the subject 12 and determines on the basis of a detected light a point in time when the cardiac pulse reaches the skin of the subject 12. The light detection device 18 provides a corresponding second signal to the processing unit 24. The light detection device 18 is preferably formed as a photoplethysmography sensor and determines the point in time when the cardiac pulse reaches the skin on the basis of an intensity or a color of the light received from the skin of the subject 12.

The processing unit 24 evaluates the first signal received from the ultrasound transducer 16 and the second signal received from the light detection device 18 and determines a time delay between the cardiac pulse determined by the ultrasound transducer 16 and the cardiac pulse determined by the light detection device 18 and determines a pulse transit time between the cardiac pulse in the artery and the point in time when the cardiac pulse reaches the skin based on the light detection. The processing unit 24 further determines a blood pressure of the subject on the basis of the pulse transit time between the first and the second signal.

Hence, the monitoring apparatus 10 is adapted to monitor the blood pressure of the subject 12 non-invasively without an obstructive cuff.

Since the measurement unit 14 is formed as a single patch including the ultrasound transducer 16 and the light detection device 18, the first signal and the second signal are measured at a single site or at neighbored portions of the subject 12 so that no additional sensors or cables are required and the influence of other parameters influencing the pulse transit time can be minimized. Further, since the measurement unit 14 can be attached to the subject's skin, the monitoring apparatus 10 can be easily used for longer duration.

It shall be understood that the controller 22 and the processing unit 24 may also be included in the measurement unit 14 and may comprise a storage device for storing the determined vital sign information and for a delayed transmission of the determined vital sign information.

Figure 2:
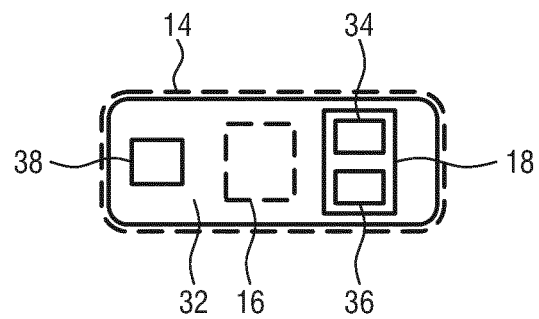
FIG. 2 shows a schematic diagram of a measurement unit of the monitoring apparatus.

FIG. 2 shows a schematic diagram of the measurement unit 14. The measurement unit 14 comprises a single base layer 32 which comprises a glue layer for attaching the measurement device 14 to the skin of the subject 12. The base layer 32 may be formed as an ultrasound-compatible hydrogel sheet including a skin-friendly glue for attaching the base layer 32 to the skin of the subject 12. The measurement unit 14 comprises the ultrasound transducer 16, the light detection device 18 including a light sensor 34 for detecting the light received from the subject 12 and for providing the second signal on the basis of the received light and a light source 36 for emitting light to the subject 12, wherein the light sensor 34 is adapted to detect the light of the light source reflected by the subject 12. The light detection device 18 is preferably formed as a photoplethysmography sensor and provides the second signal as a photoplethysmography signal to the processing unit 24. The light sensor 34 is preferably formed as a photodiode and the light source 36 is preferably formed as a light emitting diode.

The measurement unit 14 further comprises an accelerometer device 38 for measuring a posture of the measurement unit 14 or the subject 12 and for determining an angle of an artery 30 with respect to the gravity. The accelerometer device 38 may further be adapted to determine a movement of the measurement unit 14 and/or the artery 30. The accelerometer device 38 further determines corresponding changes of the posture of the measurement unit 14 or the subject 12. The accelerometer device 38 provides a third signal to the processing unit 24, wherein the processing unit 24 provides a calibration of the determined vital sign information on the basis of the posture of the measurement unit 14 or the subject 12 or the artery 30 with respect to the gravity and the changes thereof and/or the movement of the artery 30. The processing unit 24 may also ignore or omit measurements which are potentially corrupted by strong movement artifacts so that erroneous measurements can be avoided. The accelerometer device 38 may be formed as a gyroscope and is also attached to the base layer 32 as shown in FIG. 2.

Further, a vascular stiffness or an arterial stiffness of the artery 30 can be determined on the basis of a difference between the two time delays or the two pulse transit times PTT.

Finally, the different pulse transit times PTT, the arterial stiffness, the posture of the subject 12 or the artery 30, the waveform features of the first and the second signal, and in particular patient demographics are input parameters of the processing unit 24, which determines the blood pressure on the basis of a blood pressure model and these input parameters.

The base layer 32 may further include a transmission unit for transmitting the signals to the control unit 20 or may be connected by means of a wire to the processing unit 24. The base layer 32 may further comprise a storage unit for storing the measured signals and for transmitting the signals in a delayed manner.

The glue layer is disposed e.g. as a semi-solid hydrogel interface as an acoustic interface between the ultrasound transducer 16 and the skin of the subject 12. A skin-friendly glue layer, e.g. hydrophilic silicone around the sensors as well as the whole base layer 32 ensure a proper contact between the ultrasound transducer 16 an the light detection device 18 and the skin of the subject 12 during the monitoring process. The glue layer may be optically transparent in order to transmit the light from and to the light detection device 18. Alternatively, an opening in the glue layer may be formed for the light detection device 18.

The base layer 32 may further comprise a pressure-inducing layer or one or more pressure transducer, which can increase and decrease the pressure by means of which the base layer 32 is contacted to the skin of the subject 12. The pressure inducing layer may be an inflating air bed or an electroactive actuator or another actuator which is connected to a top of the base layer 32. The processing unit 24 forms a feedback loop in order to optimize the signals received from the ultrasound transducer 16 and the light detecting device 18 and correspondingly increases or decreases the contact force or an angle of the contact force applied by the pressure inducing layer.

In a preferred embodiment, one pressure transducer is be placed on top of both sensors, the ultrasound transducer 16 and the light sensor 18. Alternatively, two transducers can be placed on each of the sensors individually, or only one sensor can be equipped with a pressure transducer. The pressure transducers can be controlled to regulate the contact pressure and preferably also the pressure angle or the pressure distribution separately for each of the sensors based on each individual sensor signal. In the case that one pressure transducer is used for both sensors, the processing unit 24 ensures that the applied pressure is high enough to obtain a good ultrasound signal and low enough to obtain a good photoplethysmography signal.

Figure 3:
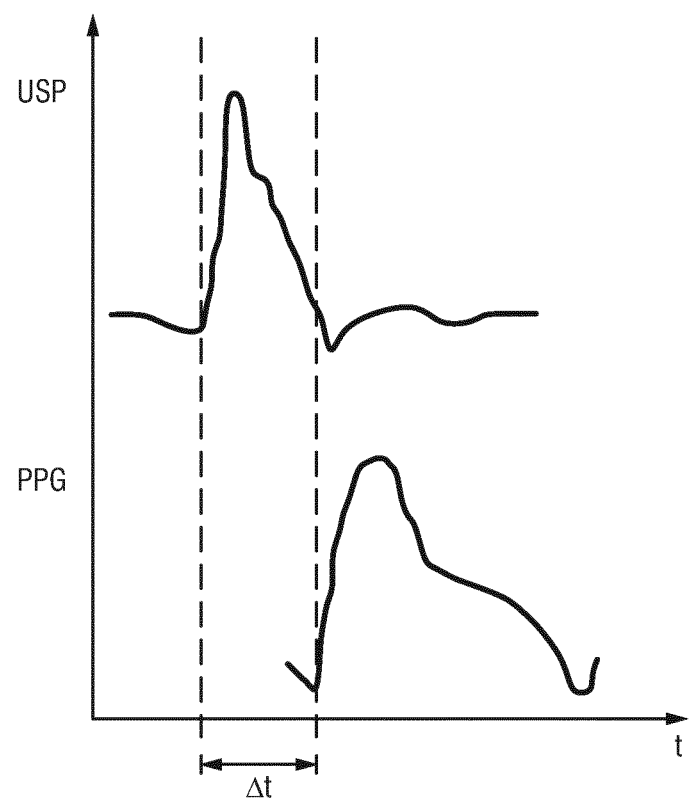
FIG. 3 shows a schematic waveform diagram of different signals provided by the measurement unit.

FIG. 3 shows a timing diagram of an ultrasound pulse wave USP measured by the ultrasound transducer 16 and a photoplethysmography pulse wave PPG measured by the light sensor 18. The processing unit 24 determines a time delay $\Delta t$ between a characteristic point in the two pulse wave signals, wherein the time delay $\Delta t$ corresponds to the pulse transit time PTT between the measured ultrasound pulse wave USP and the photoplethysmography pulse wave PPG measured at the skin of the subject 12. On the basis of the pulse transit time PTT, the processing unit 24 determines the blood pressure of the subject 12 as the vital sign information.

Further characteristics of the first and the second signal like dc level, ac amplitude, ac/dc ratio, a peak/notch ratio, a time delay between peak and notch, and features from the frequency spectrum can be measured to determine the vital sign information.

The processing unit 24 determines a peak or a foot or other features like a maximum the rising or falling slope in the ultrasound pulse wave USP and the photoplethysmography signal PPG or a specific point in a fitted function thereof and determines the time delay Δt on the basis of the so determined peak or foot or the other features of the two signals.

Hence, the pulse transit time PTT can be reliable determined on the basis of these two signals with low technical effort.

Figure 4:
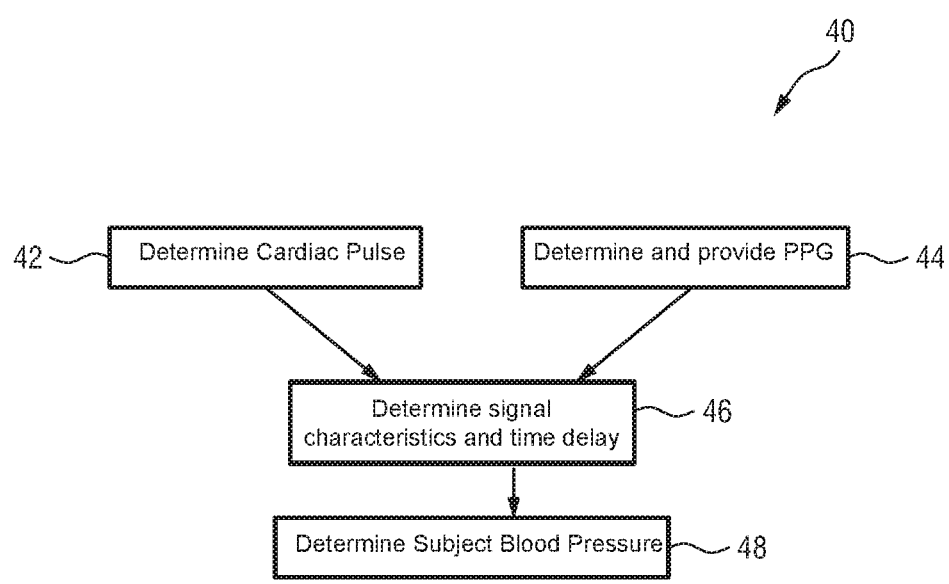
FIG. 4 shows a schematic flow diagram of a method for monitoring vital sign information of a subject.

FIG. 4 shows a schematic flow diagram of a method for monitoring the vital sign information of the subject 12. The method is in FIG. 4 generally denoted by 40.

At step 43, the ultrasound transducer 16 determines the cardiac pulse on the basis of the ultrasound wave received from the subject 12, e.g. from the artery 30 of the subject 12 and provides the ultrasound pulse wave USP as the first signal to the processing unit 24. In parallel, the light detection device 18 determines the photoplethysmography signal PPG based on the light received from the skin of the subject 12 and provides the photoplethysmography signal PPG as the second signal to the processing 24 as shown at step 44. At step 46, the processing unit 24 determines the corresponding peaks or foots or other characteristic features of the first and the second signal and determines a time delay Δt between the characteristic features as the pulse transit time PTT.

At step 48, the processing unit 24 determines the blood pressure of the subject 12 on the basis of the so determined pulse transit time PTT.

The cardiac pulse determined at step 42 can be determined on the basis of a blood flow velocity in the artery 30 derived from an ultrasound Doppler signal provided by the ultrasound transducer 16. Alternatively, the cardiac pulse and the corresponding ultrasound pulse wave USP can be determined on the basis of a movement of an arterial wall of the artery 30 on the basis of a fast sequential A-mode or B-mode image provided by the ultrasound transducer 16. In other words, the ultrasound pulse wave USP is determined on the basis of the dilation of the arterial wall of the artery 30 and compared to the photoplethysmography signal PPG.

Figure 5:
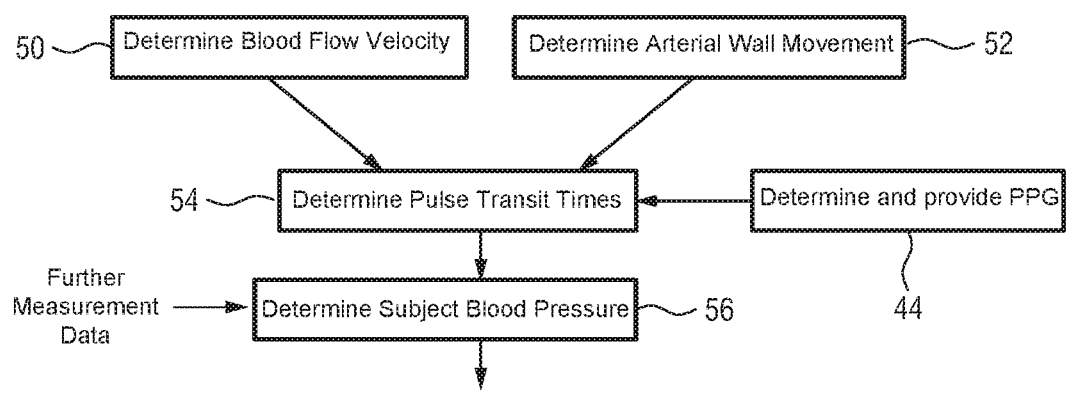
FIG. 5 shows a schematic block diagram of an embodiment of the method shown in FIG. 4.

FIG. 5 shows a schematic flow diagram of an embodiment of the method 40. At step 50, the blood flow velocity is determined on the basis of the ultrasound Doppler signal received from the ultrasound transducer 16 and at step 52, the arterial wall movement or expansion of the arterial wall is determined on the basis of the fast sequential A-mode or B-mode image signal received from the ultrasound transducer 16. At step 44, the photoplethysmography signal PPG is determined as mentioned above. At step 54, different pulse transit times are determined on the basis of the different ultrasound pulse wave signals determined at steps 50 and 52 and an average of the pulse transit times is determined. The time delays of the different ultrasound pulse wave signals to the photoplethysmography signal PPG may be weighted differently so that one of the measurements is considered more than the other.

On the basis of the so determined average pulse transit times and on the basis of further measurement data e.g. from the accelerometer or on the basis of a calibration and a blood pressure model, the blood pressure of the subject 12 is determined.

The determination of the blood pressure may be based on separate calibrations of the ultrasound pulse wave signals USP determined on the basis of the blood velocity and the arterial wall movement determined at steps 50 and 52. This is a possibility to increase the robustness of the determination of the blood pressure.

Figure 6:
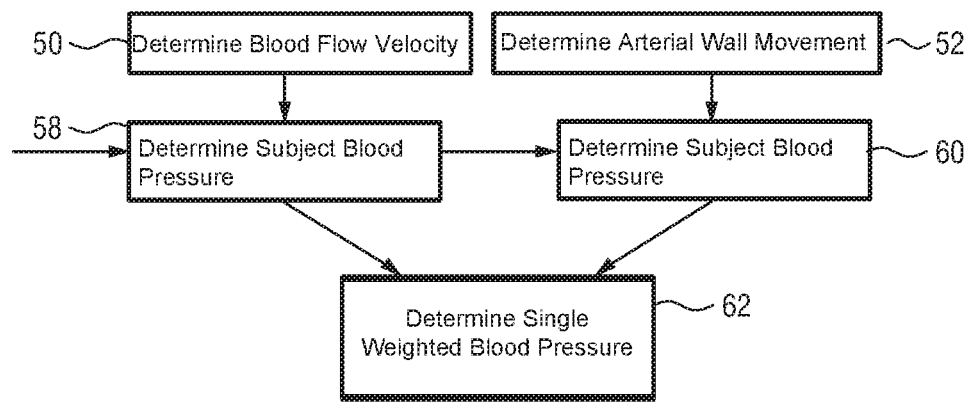
FIG. 6 shows a schematic block diagram of an embodiment of the method shown in FIG. 4.

FIG. 6 shows a schematic flow diagram of an embodiment of the method 40 for determining the vital sign information of the subject 12. At steps 50 and 52, the ultrasound pulse wave signals USP are determined as mentioned above. At steps 58 and 60 the blood pressure of the subject 12 is separately determined or estimated based on different blood pressure models and other inputs, e.g. from the accelerometer 38 and/or on the basis of different calibration and the so determined or estimated different blood pressure values are averaged or weighted at step 62 to a single blood pressure value.

Since the blood pressures values are separately determined on the basis of different models and/or calibrations at steps 58 and 60, the result of the blood pressure determination becomes more robust.

Figure 7:
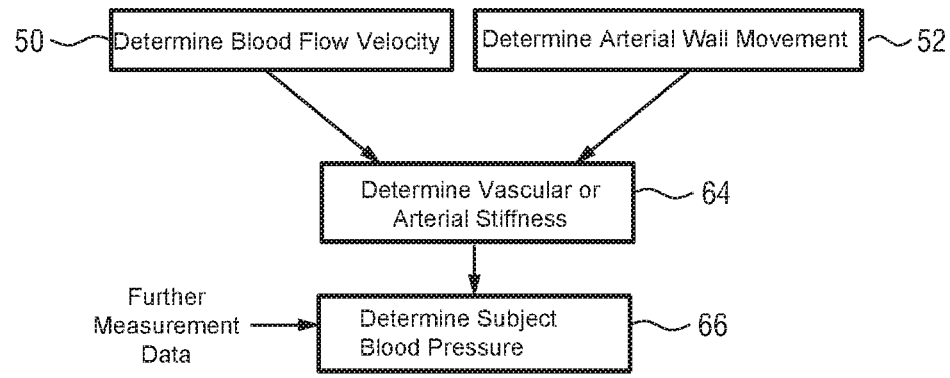
FIG. 7 shows a schematic block diagram of an embodiment of the method shown in FIG. 4.

FIG. 7 shows a schematic flow diagram of an embodiment of the method 40. The time delay and the pulse transit time PTT are determined on the basis of the blood flow velocity and the arterial wall movement at steps 50 and 52 as mentioned above. At step 64, a vascular stiffness or an arterial stiffness of the artery 30 is determined on the basis of a difference between the two time delays or the two pulse transit times PTT. The vascular or arterial stiffness is utilized to determine the blood pressure at step 66 and utilized as an input value for the blood pressure model used to determine or estimate the blood pressure of the subject 12 at step 66. As mentioned above, other input parameters, e.g. received from the accelerometer 38 or calibration values are used as input parameter of the blood pressure model.

Figure 8:
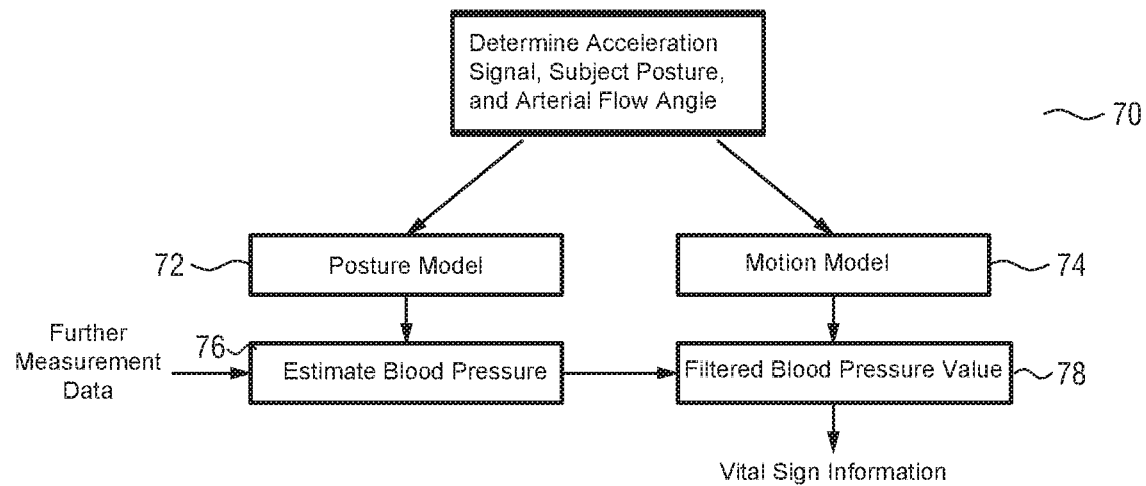
FIG. 8 shows a schematic block diagram of an embodiment of the method shown in FIG. 4.

FIG. 8 shows a schematic flow diagram of an embodiment of the method 40. At step 70, the accelerometer 38 determines an acceleration signal and the processing unit 24 determines a posture of the subject 12 and changes thereof and thereby a flow angle of the artery 30 with respect to gravity and changes thereof. The posture information is utilized in a posture model as shown at step 72 and the determined motion is utilized in a motion model as shown at step 74.

At step 76, the blood pressure is estimated based on the blood pressure model, the posture model and other inputs as mentioned above. The so determined or estimated blood pressure is utilized together with the motion model in a filtering step 78, wherein erroneous measurement values are filtered or omitted based on the detected motion of the accelerometer 38. The so filtered blood pressure value is provided as the vital sign information of the subject 12.

Figure 9:
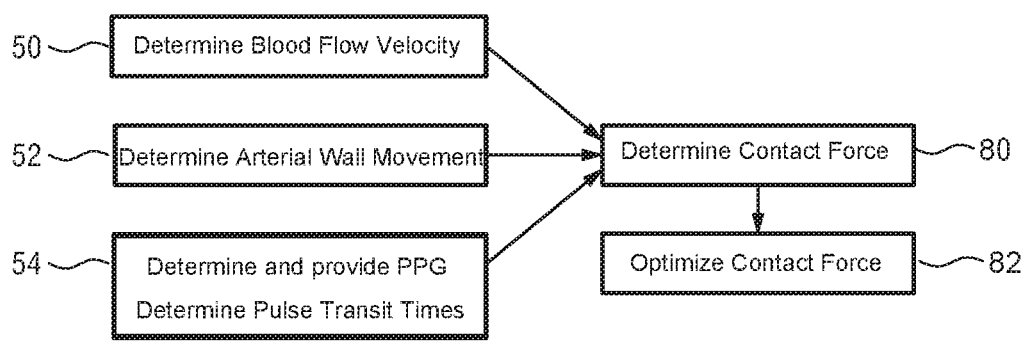
FIG. 9 shows a schematic block diagram for determining a contact quality of the measurement unit.

FIG. 9 shows a schematic flow diagram of an embodiment of the method 40. At step 50, the blood flow velocity is determined as mentioned above. At step 52, the arterial wall movement is determined as mentioned above and at step 44 the photoplethysmography signal PPG is determined as mentioned above. A contact force is determined on the basis of the measurement signals determined at steps 50, 52, and 54 as shown at step 80. The contact force of the base layer 32 to the skin of the subject 12 can be determined on the basis of the different measurement signals and the respective contact quality can be determined at step 80. At step 82, the contact force between the base layer 32 and the skin of the subject 12 is optimized by means of the pressure inducing layer attached to the base layer 32 such as an inflating air bed or electro-active actuators or other actuators on the top of the base layer 32. The contact force is optimized at step 82.

In detail, when the total reflected ultrasound energy is reduced, the contact force is increased at step 82 and if the blood flow signal determined at steps 50, 52, and 54 is reduced, the contact force is too large and closes the artery 30 so that the contact force between the base layer 32 and the skin of the subject 12 is reduced at step 82.

The processing unit 24 which forms a feedback loop optimizes a function $$J(P,V)=f(P)+g(V)$$

wherein P is the ultrasound energy, V is the blood flow signal and f and g are monotonically increasing functions. For example, $J(P,V)=P+\lambda V$ for $\lambda>0$. The parameter $\lambda$ is used to compensate a difference of scaling of P and V. The gain dV/dF depends on the depth of the artery 30 and the tissue compensation, e.g. by muscles or fat, and the gain dP/dF depends on, e.g., an amount of contact (hydro)gel and the skin thickness.

Hence, the contact of the base layer 32 can be automatically optimized so that the quality of the signals and the respective measurements can be continuously maintained.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. A controller (including any equivalent means), implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Any reference signs in the claims should not be construed as limiting the scope.

The invention claimed is:

1. A monitoring apparatus for monitoring a blood pressure of a subject, comprising:
    a measurement unit comprising: an ultrasound transducer for emitting ultrasound waves to a volume of the subject that includes a blood vessel and for receiving ultrasound waves from said volume of the subject, and for providing a first signal on the basis of ultrasound waves received from the volume of the subject; and;
    a light source for emitting light to the subject and a light sensor for detecting emitted light received from the subject and for providing a second signal on the basis of light received from skin of the subject, and
    a processing unit which is configured to:
        determine a time of arrival of a cardiac pulse in the blood vessel based on the first signal,
        determine a point in time when the cardiac pulse reaches the skin of the subject based on the second signal,
        and determine a pulse transit time between the time of arrival of the cardiac pulse in the blood vessel and the point in time when the cardiac pulse reaches the skin of the subject; and
    wherein the measurement unit has a common base layer to which the ultrasound transducer and the light sensor are attached, the common base layer having a pressure-inducing layer or one or more pressure transducers arranged to increase and decrease a pressure of the common base layer on the skin of the subject, wherein the processing unit is configured to control the pressure-inducing layer or the one or more pressure transducers;
    wherein the processing unit is configured to determine the blood pressure based on the pulse transit time; and to provide optimum contact of the base layer to the skin of the subject by forming a feedback loop responsive to the first signal and the second signal to determine and apply the pressure of the common base layer at a level such as to optimize the contact.

2. The monitoring apparatus as claimed in claim 1, wherein the light sensor is a photoplethysmography sensor for providing a photoplethysmography signal (PPG) as the second signal.

3. The monitoring apparatus as claimed in claim 1, wherein the light source is adapted to emit light having different wavelengths and wherein the light sensor is adapted to detect wavelengths backscattered by a portion of the subject.

4. The monitoring apparatus as claimed in claim 1, wherein the ultrasound transducer is adapted to provide a blood velocity signal corresponding to a blood velocity in the volume of the subject on the basis of the ultrasound waves received from the subject as the first signal.

5. The monitoring apparatus as claimed in claim 1, wherein the ultrasound transducer is adapted to provide a movement signal corresponding to a movement of an anatomical feature in the volume of the subject as the first signal.

6. The monitoring apparatus as claimed in claim 4, wherein the processing unit is adapted to determine an arterial stiffness on the basis of the blood velocity and a movement of an anatomical feature in the volume of the subject as the first signal.

7. The monitoring apparatus as claimed in claim 1, wherein the processing unit is adapted to determine blood pressure on the basis of the pulse transit time and on the basis of a calibration function.

8. The monitoring apparatus as claimed in claim 1, wherein the processing unit is configured to transmit blood pressure information to a base unit.

9. The monitoring apparatus as claimed in claim 1, the measurement unit further comprising a detector for detecting a motion and/or an orientation of the measurement unit and/or the subject, wherein the processing unit is adapted to determine blood pressure information further on the basis of the detected motion and/or the detected orientation.

10. The monitoring apparatus as claimed in claim 1, wherein the base layer further comprises a glue layer or an adhesive layer for attaching the measurement unit to the skin of the subject.

11. The monitoring apparatus as claimed in claim 1, wherein the pressure-inducing layer or the one or more pressure transducers are arranged to regulate a pressure angle or a pressure distribution of the ultrasound transducer and/or the light sensor.

12. A monitoring method for determining a blood pressure of a subject, comprising the steps of:
   providing a measurement unit comprising an ultrasound transducer and a light detection unit configured to be used on skin of the subject to determine a first signal on the basis of ultrasound waves received from a volume of the subject that includes a blood vessel;
   determining a second signal on the basis of light received from the skin of the subject;
   determining a time of arrival of a cardiac pulse in the blood vessel based on the first signal;
   determining a point in time when the cardiac pulse reaches the skin of the subject based on the second signal;
   determining a pulse transit time between the time of arrival of the cardiac pulse in the blood vessel and the point in time when the cardiac pulse reaches the skin of the subject;
   determining the blood pressure based on the pulse transit time; and
   providing optimum contact of the measurement unit to the skin of the subject by forming a feedback loop responsive to the first signal and the second signal to determine a pressure between the measurement unit and the skin of the subject at a level such as to optimize the contact and applying the pressure between the measurement unit and the skin of the subject at the level such as to optimize the contact.

13. The monitoring method of claim 12, further comprising the steps of:
   providing a blood velocity signal corresponding to a blood velocity in the volume of the subject on the basis of the ultrasound waves received from the subject as the first signal;
   providing a movement signal corresponding to a movement of an anatomical feature in the volume of the subject as the first signal; and
   determining an arterial stiffness on the basis of the blood velocity and the movement signal.

14. A computer program product for determining the blood pressure of a subject, the computer program product comprising non-transitory computer-readable program code downloadable from a communications network, or storable on, or stored on a computer-readable storage medium, which computer-readable program code, when run on a computer, causes the computer and an associated measurement unit to perform all the steps of claim 12.

15. The monitoring method of claim 12, further comprising the step of regulating a pressure angle or a pressure distribution of the ultrasound transducer and/or the light sensor with the pressure-inducing layer or the one or more pressure transducers.

* * * * *